US00PP21414P2

(12) United States Plant Patent
Gargiulo

(10) Patent No.: US PP21,414 P2
(45) Date of Patent: Oct. 26, 2010

(54) GRAPEVINE PLANT NAMED 'VISTA'
(50) Latin Name: *Vitis vinifera*
Varietal Denomination: Vista

(75) Inventor: Angel A. Gargiulo, Godoy Cruz (AR)
(73) Assignee: M.Caratan, Inc., Delano, CA (US)

( * ) Notice: Subject to any disclaimer, the term of this patent is extended or adjusted under 35 U.S.C. 154(b) by 0 days.
(21) Appl. No.: 12/586,500
(22) Filed: Sep. 23, 2009
(51) Int. Cl.
*A01H 5/00* (2006.01)
(52) U.S. Cl. ..... Plt./207
(58) Field of Classification Search ..... Plt./207
See application file for complete search history.

*Primary Examiner*—Annette H Para
(74) *Attorney, Agent, or Firm*—Jondle & Associates, P.C.

(57) ABSTRACT

A new and distinct grapevine plant particularly distinguished by having green, large, seedless berries, with flavor characteristics described as sweet and neutral, is disclosed.

7 Drawing Sheets

Genus and species: *Vitis vinifera.*
Variety denomination: 'Vista'.

BACKGROUND OF THE NEW PLANT

The present invention comprises a new and distinct cultivar of grapevine botanically known as *Vitis vinifera* and hereinafter referred to the cultivar name as grapevine 'Vista'. The new cultivar originated from a cross conducted in May 1992 in Delano, Calif. between the proprietary female grapevine plant 'C.G.33.771' (unpatented) and the proprietary male parent 'C.G.73.302' (unpatented). The seeds produced from the cross were subsequently planted in 1993 in Delano, Calif. A single plant selection was chosen for further asexual propagation in January 2004 in Delano, Calif.

The new cultivar has been asexually reproduced repeatedly by vegetative cuttings in Delano, Calif. over a five and one-half year period.

The present invention has been found to retain its distinctive characteristics through successive asexual propagations.

SUMMARY OF THE INVENTION

The following are the most outstanding and distinguishing characteristics of this new cultivar when grown under normal horticultural practices in Delano, Calif.:

1. Large, green seedless berries; and
2. Flavor characteristics described as sweet and neutral.

DESCRIPTION OF THE PHOTOGRAPHS

This new grapevine plant is illustrated by the accompanying photographs which show clusters of fruit thereof, leaves, canes, tendrils and berries. The colors shown are as true as can be reasonably obtained by conventional photographic procedures. The photographs are taken from a plant about 5 years old, grown in a field in Delano, Calif. in 2009 at bloom and at harvest.

Figure 1:
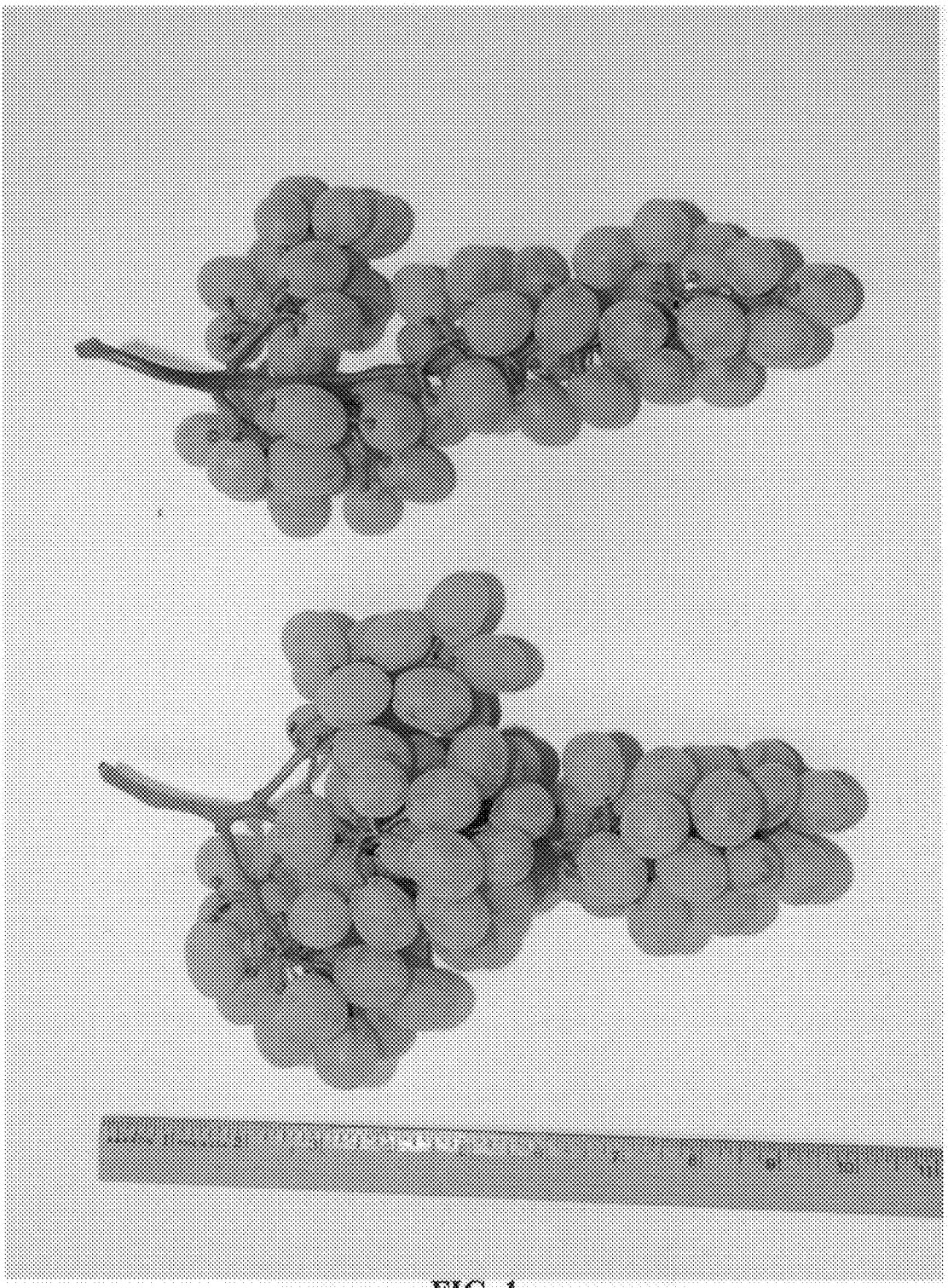
Figure 2:
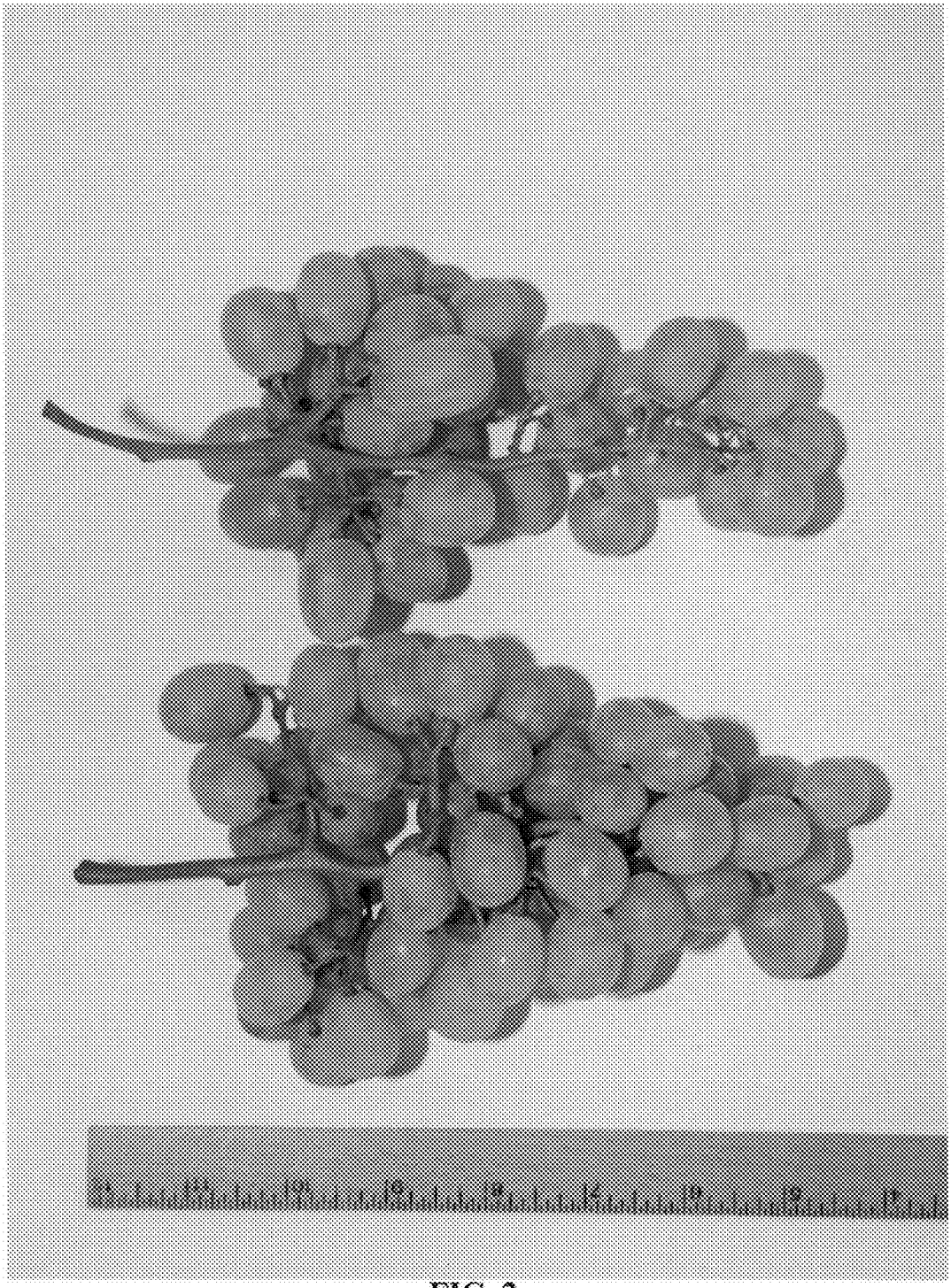
Figure 3:
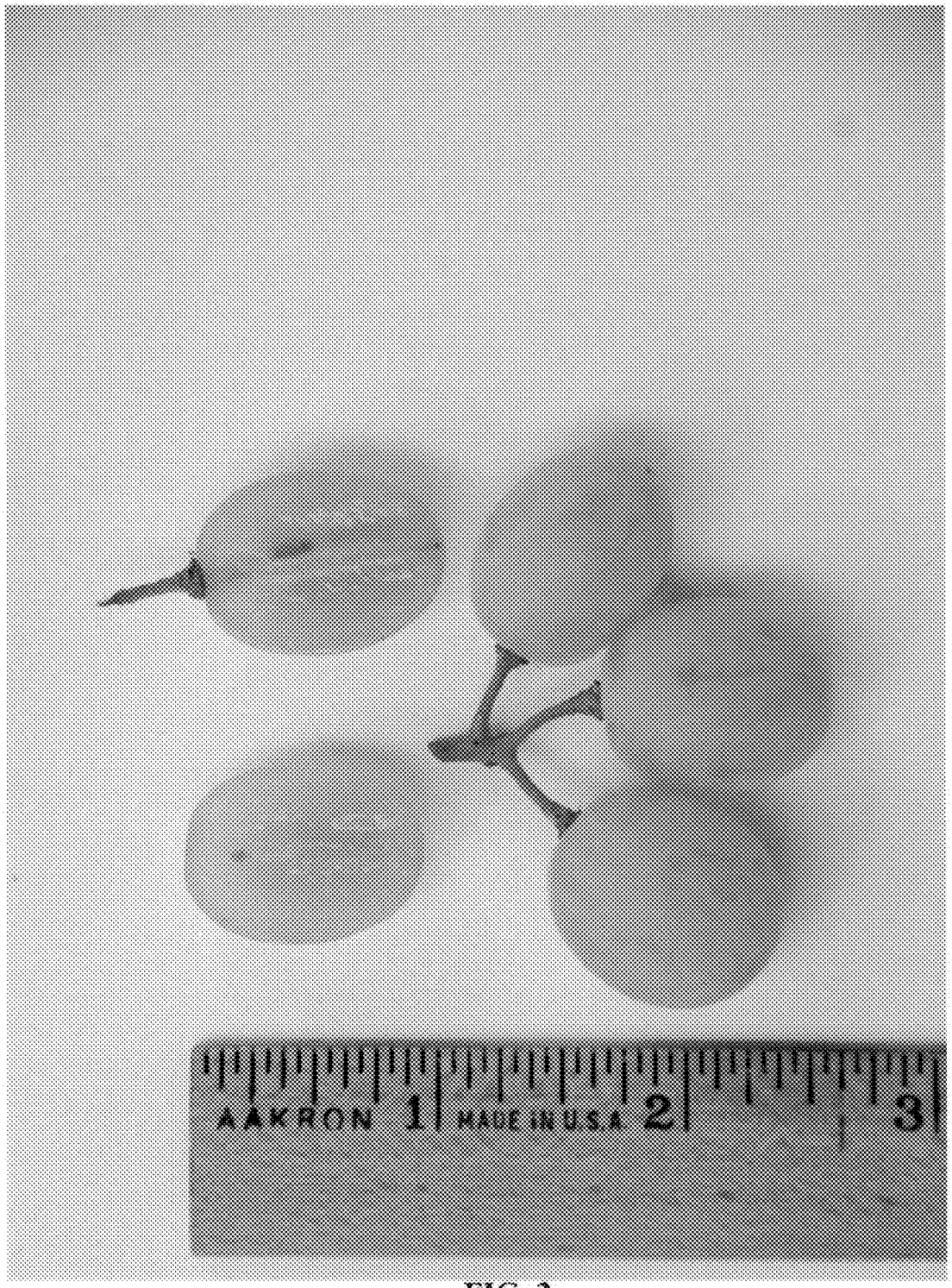
Figure 4:
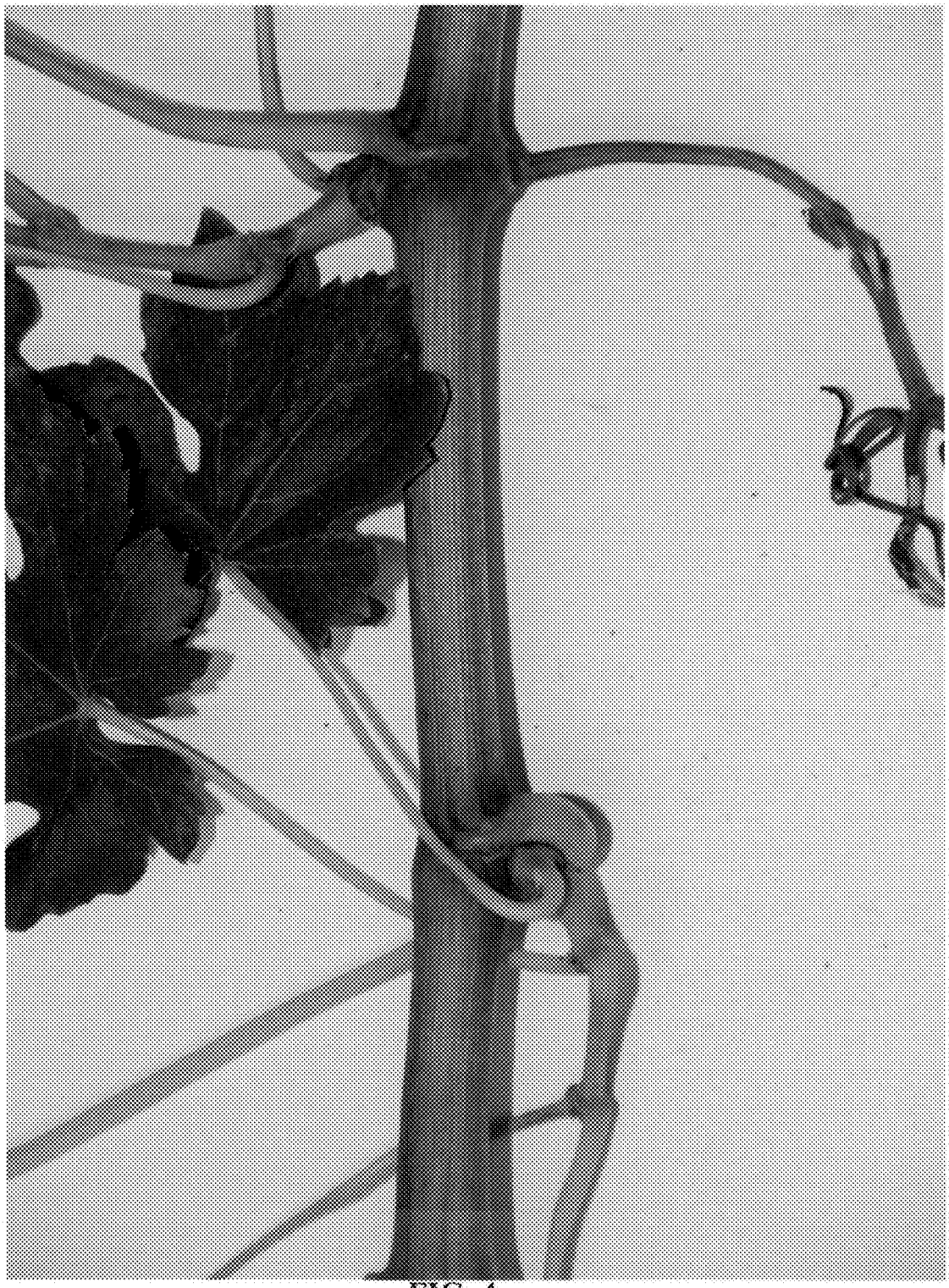
Figure 5:
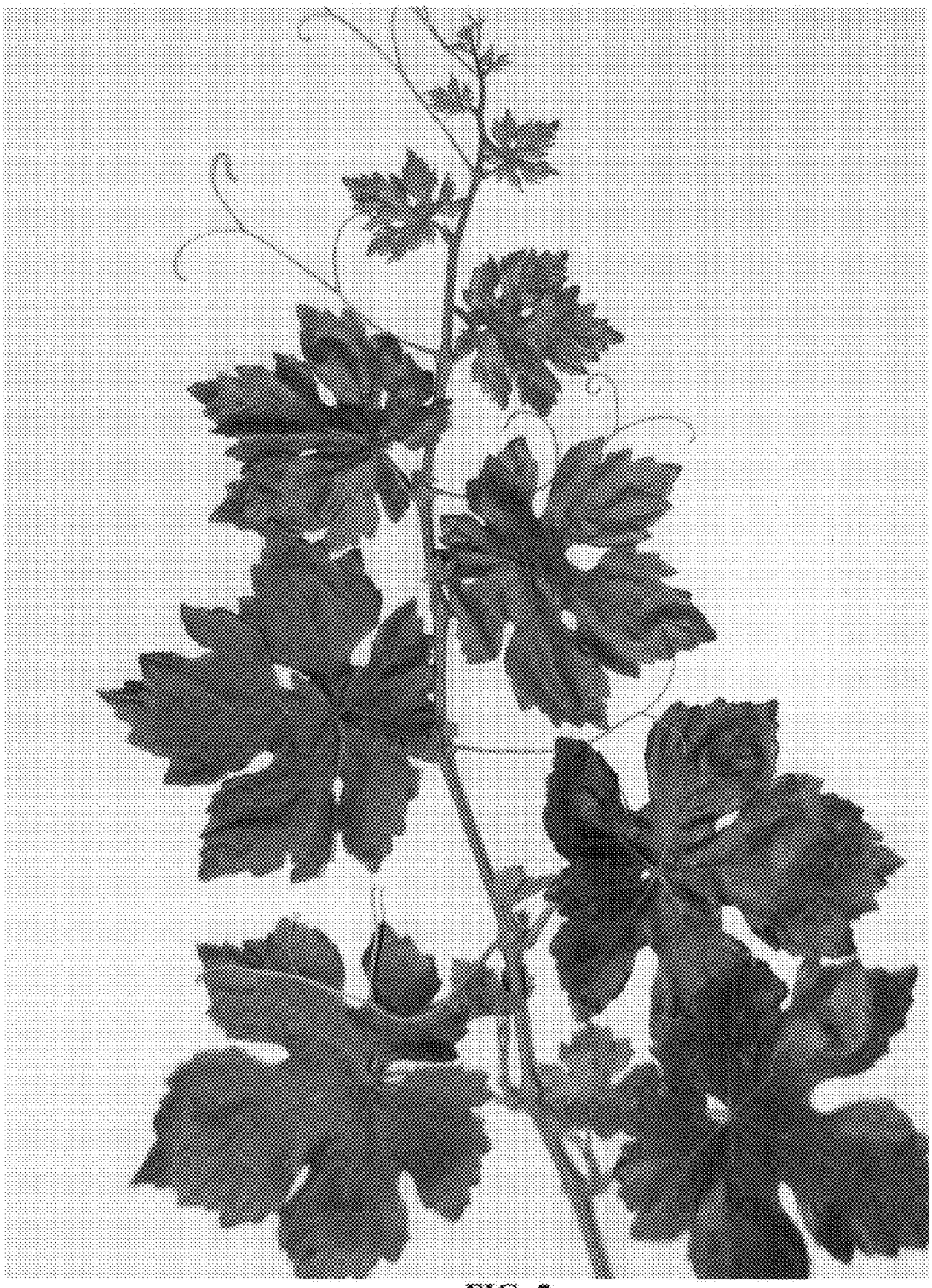
Figure 6:
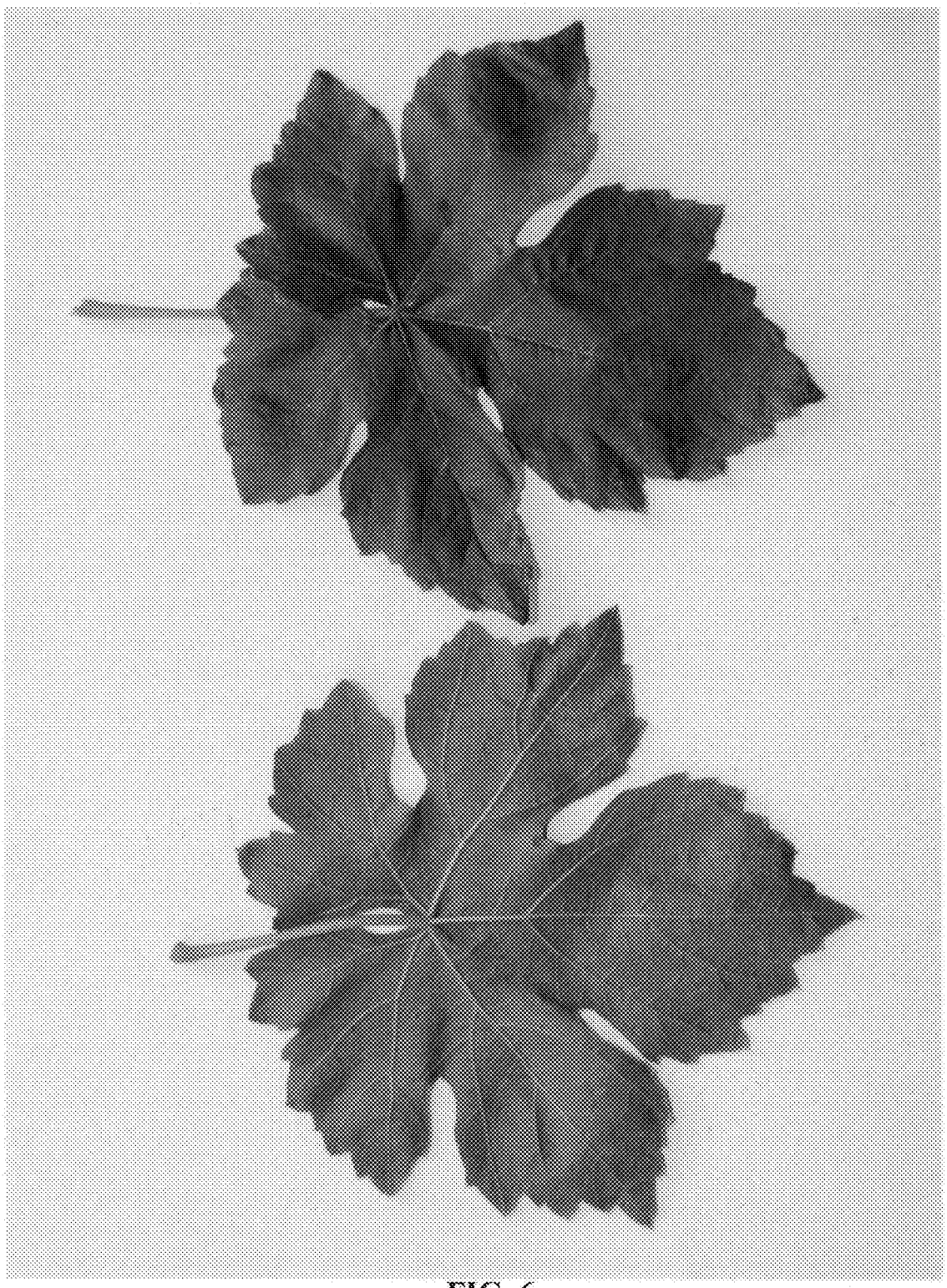
Figure 7:
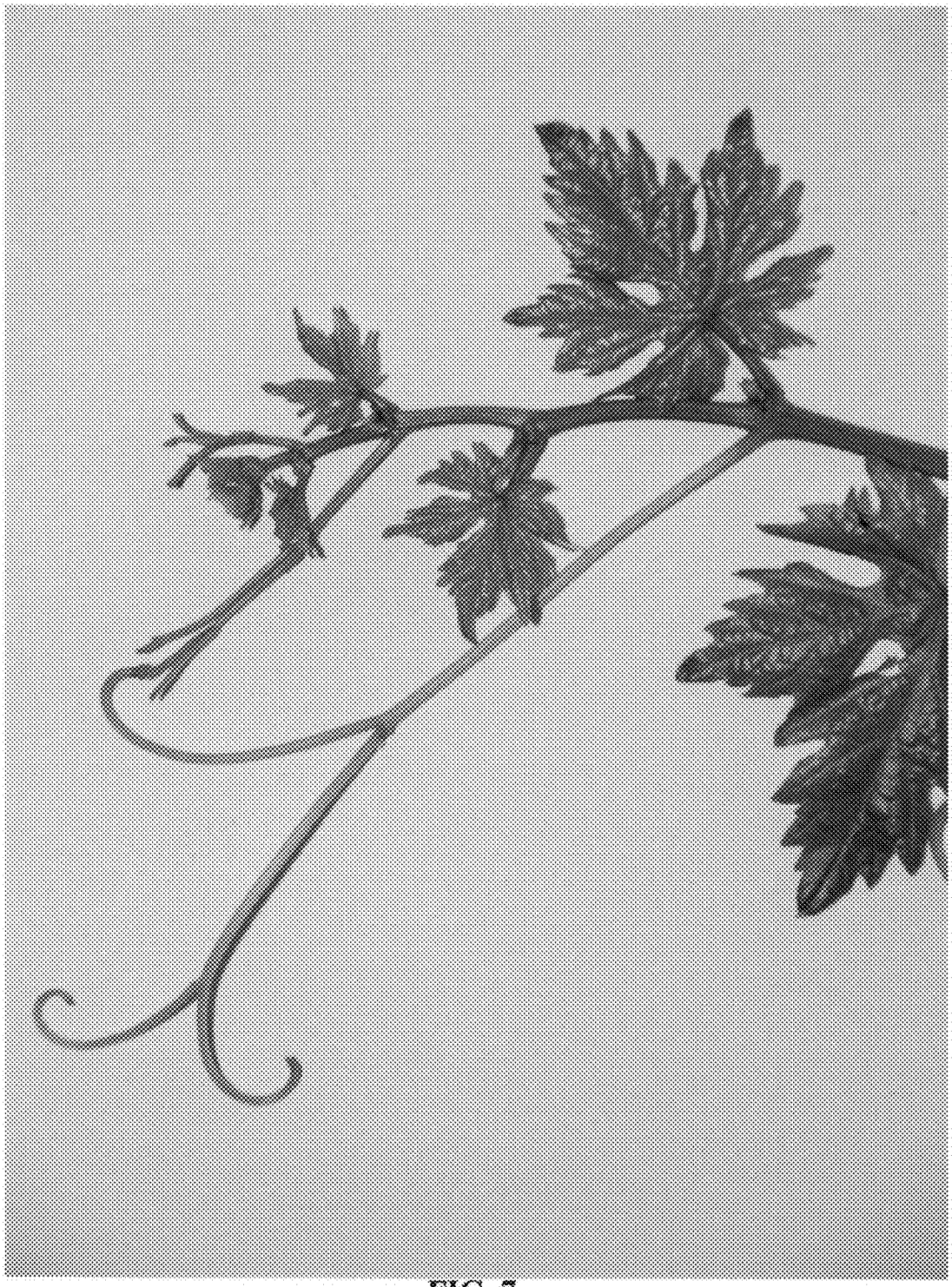

FIG. 1 shows a close-up of a primary cluster of berries at harvest.
FIG. 2 shows a secondary cluster of berries at harvest.
FIG. 3 shows a close-up of the berries at harvest.
FIG. 4 shows a mature shoot (cane) section at harvest.
FIG. 5 shows a primary shoot (cane) at bloom.
FIG. 6 shows a close-up of the mature leaves at bloom.
FIG. 7 shows a growing shoot tip at bloom.

DESCRIPTION OF THE NEW CULTIVAR

The following detailed description sets forth the distinctive characteristics of 'Vista'. The data which defines these characteristics were collected from asexual reproductions carried out in Delano, Calif. The plant history was taken on 5 year old grapevines grown under field conditions in Delano, Calif. All color references were obtained under natural light. All major color code designations are by reference to Munsell Color Charts for Plant Tissues by Munsell Color, 617 Little Britain Rd., New Windsor, N.Y. 12553-6148. Common color names are also occasionally employed. For the distribution of the tendrils, please refer to publication "Grape Varieties and Rootstock Varieties" by Pierre Galet, 1998 English Edition, Oenoplurimedia sarl, Chateau de Chaintre, 71570 Chaintre, France (where tendril distribution is intermittent, 0s, 1s and 2s are referred to as follows: 0 is a node without a tendril; 2 refers to 2 nodes in a row with a tendril; and 1 is a single node with a tendril).

DETAILED BOTANICAL DESCRIPTION OF THE NEW PLANT

Classification:
- *Family.*—Vitaceae.
- *Botanical name.*—*Vitis vinifera.*
- *Variety name.*—'Vista'.

Plant:
- *Plant habit and growth.*—Trailing with moderate secondary shoot development.
- *Time to maturity.*—4 years.
- *Height* (*at maturity*).—Cordon at 132.08 cm; canopy is 215.9 cm high.
- *Width* (*at maturity*).—Canopy is 203.2 cm wide.
- *Vigor.*—High.
- *Productivity.*—Medium.
- *Rootstock.*—Own rootstock.
- *Use.*—Fresh market table grapes.

Trunk:
- *Diameter.*—8.89 cm.
- *Surface texture.*—Coarse, rough.
- *Color.*—Exposed surface is 5YR 7/2; non-exposed (when peeled) is 5YR 5/4.

Canes:
- *Diameter*(*average*).—0.10 cm average at nodes 8-9.
- *Length* (*average*).—193.04 cm.
- *Surface texture* (*both immature and mature canes*).—Smooth.

*Form* (*woody shoot cross section form*).—Pith in center with diaphragm at nodes.

*Color* (*mature*).—7.5YR 6/4 at harvest, Aug. 18, 2009.

*Color* (*immature*).—7.5GY 8/6 at bloom, Aug. 18, 2009.

*Internode length* (*upper mature sun cane, average*).—8.76 cm.

Time of bud burst: March 20.

Tendrils:

*Form.*—Most commonly as a secondary fork with two branches borne off of a primary fork; secondarily as one primary fork with branches.

*Size.*—General: Large. Length (average): 19.05 cm on primary shoots. Diameter, main branch (average): 0.24 cm.

*Texture and distribution.*—Smooth (no pubescence); tendril distribution is intermittent, from flower cluster 0-2-0-2-0-0-2-0-2 and 1-0-0-2-0-2-0-1-0-2 about equally common; occasionally 1-0-1-0-2-0-2-0-1.

*Color* (*mature*).—2.5GY 8/6 for the $8^{th}$ tendril on node 12 from tip.

*Anthocyanin* (*both immature and mature*).—Absent.

*Color* (*immature*).—2.5GY 8/4 for $3^{rd}$ tendril from tip.

Growing tips (young shoot):

*Pubescence.*—Slight.

*Color.*—2.5GY 7/8.

*Anthocyanin.*—5R 4/4 on the youngest leaves at the tip, fading toward the $4^{th}$ leaf to no anthocyanin on leaves 5 and 6 thereafter.

*Shape.*—Slightly curved when growing rapidly.

*Apex.*—Normal, triangular.

Leaves:

*Shape.*—Cordiform (heart shaped); inferior lateral sinuses and superior lateral sinuses deep with a close 1:1 length to width ratio.

*Apex.*—Pointed.

*Base.*—Rounded.

*Margin.*—Teeth irregular.

*Height of teeth on margin* (*average*).—0.28 cm (ranges from 0.1 cm to 0.8 cm; height/width ratio is about 0.28 (ranges from 0.12 to 0.44).

*Shape of teeth on margin.*—Wide teeth with convex sides.

*Texture* (*mature leaf*).—Upper surface: Smooth to slightly bullate; glabrous. Lower surface: Smooth; almost glabrous with sparse short hairs on veins.

*Immature leaf.*—Length: 7.62 cm at about 14 days of age, $5^{th}$ leaf from tip. Width: 7.37 cm at about 14 days of age, $5^{th}$ leaf from tip. Color, upper surface: 2.5GY 6/8. Color, lower surface: 2.5GY 6/8.

*Mature leaf.*—Length: 18.03 cm at node 8. Width: 18.29 cm at node 8. Color, upper surface: 5GY 4/6. Color, lower surface: 5GY 6/6.

*Venation.*—Pattern: Primary and secondary veins on the upper surface are visible due to their lighter color contrasting with the interveinal tissue; the lower surface veins are raised. Color (both upper and lower surfaces): 2.5GY 7/6.

*Petiolar sinus.*—Narrow lyre-shaped; often slightly overlapping.

*Petiole.*—Length: 11.68 cm average. Diameter: 0.375 cm. Color: 7.5GY 6/6.

Floral cluster:

*General description and location.*—Medium-sized, not shouldered and occasionally with a tendril borne on the peduncle; primary clusters are mostly positioned on node 4, occasionally on node 5; secondary clusters are positioned on node 5. Quantity of inflorescences per cluster (average): 245 (ranges from 125 to 505).

*Length* (*average, not including the peduncle*).—16.13 cm.

*Width* (*average*).—11.68 cm.

*Peduncle length* (*average*).—4.65 cm.

*Inflorescences.*—Hermaphroditic.

*Stamens.*—Medium length and straight.

*Anthers* (*color*).—Cream-colored to yellowish-brown.

*Date of bloom.*—67% bloom on May 8.

*Pollen amount.*—Moderate.

*Calyptra.*—Slightly segmented.

*Calyptra color.*—5GY 6/4, becoming lighter, 2.5GY 8/6 at the apex.

Fruit:

*Time of year of commercial harvest and shipment.*—Harvest: August 18.

*Cluster* (*primary bunches*).—General size: Medium, average is 0.88 lb in 2009. Length (without peduncle): 17.15 cm. Width: 14.86 cm. Density: Loose to medium. Peduncle length: 5.56 cm. Peduncle diameter: 0.47 cm. Peduncle color: 2.5GY 6/6. Number of berries per cluster (average): 75 berries. Berry: Size: Medium-large, average 5.36 grams in 2009. Shape: Obovoid to cylindrical, occasionally round. Uniformity: Good. Brix content: 20.9%. Diameter: 2.0 cm. Length: 2.5 cm. Skin color: 2.5GY 8/6. Pedicel: Length: 0.95 cm. Diameter: 0.25 cm. Color: 2.5GY 6/6. Strength of attachment to berry: Very good.

*Cluster* (*secondary bunches*).—General size: Medium-small; average is 0.31 lb. in 2009. Length (average without peduncle): 12.55 cm. Width (average): 10.0 cm. Density: Mostly loose. Peduncle length: 3.43 cm. Peduncle diameter: 0.37 cm. Peduncle color: 2.5GY 6/6. Number of berries per cluster (average): 30 berries.

*Berry.*—Size: Medium-large; average 4.63 grams in 2009. Shape: Obovoid to cylindrical, occasionally round. Uniformity: Good. Brix content: 20.3%. Diameter: 1.86 cm. Length: 2.3 cm. Skin color: 2.5GY 8/6. Pedicel: Length: 1.05 cm. Diameter: 0.145 cm. Color: 2.5GY 6/6. Strength of attachment to berry: Very good.

Berry flesh:

*Color.*—2.5GY 7/6.

*Juice, color.*—Clear.

*Juice production.*—Low-medium.

*Thickness of skin.*—Medium.

*Flavor.*—Sweet and neutral.

*Fragrance.*—Absent.

*Texture.*—Firm.

Fruit and seed set: Seed traces are very small, seeds are less than 0.2 cm to 0.3 cm long and are soft and green when present.

Disease and insect resistance: No particular resistance or susceptibility has been observed. Normal disease control practices can be used.

COMPARISON WITH PARENTAL AND COMMERCIAL CULTIVARS

'Vista' differs from the commercial cultivar 'Thompson Seedless' (unpatented) in that 'Vista' has a medium large berry size, while 'Thompson Seedless' has a medium berry size. Additionally, 'Vista' matures two weeks later than 'Thompson Seedless'.

I claim:

1. A new and distinct cultivar of grapevine plant as shown and described herein.

* * * * *